United States Patent [19]
Martin et al.

[11] Patent Number: 6,000,916
[45] Date of Patent: Dec. 14, 1999

[54] PUMP HEAD QUICK CONNECT ASSEMBLY

[75] Inventors: John T. Martin, Portland, Oreg.; Derrick S. Levanen, Hancock, Mich.

[73] Assignee: Optimize Technologies, Inc., Oregon City, Oreg.

[21] Appl. No.: 09/019,790

[22] Filed: Feb. 6, 1998

[51] Int. Cl.[6] ...................................................... F04B 39/14
[52] U.S. Cl. ............................ 417/360; 417/454; 92/128
[58] Field of Search .................................. 417/360, 454; 92/128

[56] References Cited

U.S. PATENT DOCUMENTS

| | | |
|---|---|---|
| 221,794 | 11/1879 | Dawson . |
| 3,627,358 | 12/1971 | Polston . |
| 3,958,898 | 5/1976 | Abrahams et al. . |
| 4,311,440 | 1/1982 | Eberhardt ............................ 417/360 |
| 5,172,942 | 12/1992 | Dillmann . |
| 5,572,920 | 11/1996 | Kennedy et al. ........................ 92/128 |

OTHER PUBLICATIONS

Pictorial and written description of Commercially available pump head fitting sold by Gilson/Rainin, date prior to Feb. 6, 1998.

Pictorial and written description of Commercially available pump head fitting sold by Shimadzu, date prior to Feb. 6, 1998.

*Primary Examiner*—Charles G. Freay
*Assistant Examiner*—Ehud Gartenberg
*Attorney, Agent, or Firm*—Christensen O'Connor Johnson & Kindness PLLC

[57] ABSTRACT

A pump head quick connect assembly (10) includes a pump head (28) having a body (30) penetrated by a first locating pin (16), having a proximal end (18) and a distal end (20), and a second locating pin (22), having a proximal end (24) and a distal end (26). The proximal ends of the first and second locating pins are attached to a base plate (12). The first locating pin distal end and the second locating pin distal end project beyond the pump head body and are inserted into a first outer passage (48) and a second outer passage (50), respectively, defined by a face plate (70). The face plate further defines an internally-threaded center passage (52) that threadably receives a manually adjustable screw (38). As the center screw is tightened against the pump head body, the pump head body is forced against the base plate, thereby forming a seal and centering the pump head on the base plate to prevent cocking. Loosening this single screw permits the face plate and the pump head body to be quickly removed from the locating pins.

20 Claims, 4 Drawing Sheets

PUMP HEAD QUICK CONNECT ASSEMBLY

FIELD OF THE INVENTION

The present invention relates to pumps used in analytical chemical instruments, particularly to means for connecting pump heads to their supporting structure.

BACKGROUND OF THE INVENTION

Several types of chemical analytical equipment utilize a pump to propel the analyte through the equipment. For example, a pump is utilized to pump the analyte through a high performance liquid chromatography (HPLC) column and any attached equipment, such as a guard column. Pumps used in chemical analytical equipment often utilize a reciprocating piston that is housed external to the pump housing within a pump head assembly. With the passage of time, the piston may malfunction or, more commonly, the seals within and around the pump head become worn. Consequently, it is desirable that the pump head assembly be designed so that it is easily and quickly removable in order to facilitate repair or replacement of worn or broken parts.

Additionally, it is desirable that the pump head assembly be designed to avoid cocking when the pump head is tightened against the pump housing. Cocking occurs when force is unevenly applied to the pump head as it is tightened against the pump housing, thereby causing an uneven seal between the pump head and the pump housing and a potential misalignment between the piston and piston cavity including the seal guide and fluid chamber. For example, most manufacturers mount the pump head to the pump housing by means of two bolts that penetrate the pump head body and which are threadably inserted into the pump body. The bolts are individually tightened, and if one bolt is tightened more than the other then the uneven force applied to the pump head may cause cocking.

One conventional approach to prevent cocking in a pump head assembly is to externally mount a bracket over the pump head. The bracket does not directly contact the pump head, but includes a centrally-located set screw that is tightened against the pump head to ensure a seal between the pump head and the housing of the pump. This design avoids cocking, by centrally applying a compressive force so that it is evenly distributed across the pump head surface that contacts the pump housing. Removal of the pump head can also be completed more rapidly. A drawback to this design, however, is the requirement for two brackets; the bracket mounted over the pump head, and a support bracket, attached to the pump housing, which engages the bracket mounted over the pump head. Thus, this type of pump head securement cannot be readily applied to convert existing pumps. To date, this design has been utilized only in certain HPLC systems incorporating a pump head which is secured to the piston within, so that the external bracket must first be removed, to liberate the pump and pump head assembly, before the pump head can be separated from the pump.

Another conventional solution to the problem of designing a quick release pump head assembly is to mount a cover plate over the pump head by means of two bolts which penetrate the cover plate and the pump head. The bolts are threaded into passages defined in the pump head housing. Within the pump head the bolts pass through hollow sleeves to prevent binding of the bolts to the inner surfaces of the pump head passages. The bolts support the pump head, but do not serve to directly tighten the cover plate against the pump head. The only point of contact between the cover plate and the pump head is an adjustable, centrally-located screw that penetrates the body of the cover plate. Tightening of the screw applies a force against the pump head which seals the pump head against the pump housing. Again, this design avoids cocking by centrally applying a compressive force that is evenly distributed across the pump head surface that contacts the pump body.

A drawback to this design, however, is that to remove the pump head it is necessary to first loosen the set screw and then use a wrench to unscrew and remove the two bolts that attach the cover plate to the pump head and the pump head to the pump housing. Thus this design does not provide for quick removal of the pump head. Another serious drawback to this design is that once the bolts and their hollow sleeves have been removed, the weight of the pump head is borne solely by the delicate piston located within the pump head. The piston may be broken or bent by the weight of the pump head, in which case the piston seals may also be damaged.

Further, when the pump head of conventional quick release systems is being mounted onto the pump, the pump head must be manually guided and inserted straight along the axis of the piston in order to avoid damaging the piston or the piston seals.

SUMMARY OF THE INVENTION

The present invention provides a quick connect assembly for a pump head adapted for use on analytical equipment. The quick connect assembly of the present invention includes a pump head mounted on locating pins each having a proximal end and a distal end. The proximal ends of the locating pins are attached to a base plate of a pump housing, while a fitting, including a cross member, is mounted over the distal ends of the locating pins. Tightening the fitting against the pump head forces the pump head against the base plate while centering the pump head against the base plate to avoid cocking. The fitting is easily and quickly assembled and disassembled, allowing the pump head to be easily removed from the pump by sliding the pump head off of the locating pins. The locating pins act as guides and thus the potential for damage of the piston due to off-center removal is eliminated.

In a first preferred embodiment of the present invention, the pump head quick connect assembly includes: a base plate of a pump housing; two locating pins each having a proximal end and a distal end; a pump head having a body including a first face and a second face and defining two passages; a quick connect fitting including a face plate defining two outer passages and a middle passage; and a manually adjustable finger-tight thumb screw. The proximal ends of the two locating pins are externally-threaded and are threadably received within two internally-threaded passages defined by the base plate of the pump housing. The locating pins are slidably received within the two passages longitudinally defined through the pump head body. The distal ends of the locating pins extend beyond the second face of the pump head body and are engaged within the two outer passages of the face plate. The locating pins each contains a positive stop that prevents the face plate from sliding horizontally from the pump head. The locating pins serve two purposes, both locating the pump head relative to the pump and the face plate relative to the pump head. The manually adjustable set screw is threadably inserted within the central, internally-threaded passage of the face plate. Rotation of the centrally-located thumb screw forces the pump head against the base plate, while centering the pump head against the base plate to avoid cocking. To quickly remove the pump head body, the thumb screw is loosened, the face plate is disengaged from the locating pins, and the pump head body can then be slid off of the locating pins.

In a second preferred embodiment of the present invention, the face plate includes a cam which is slidably received within a cam follower. The cam includes a cam head which is located substantially exterior to the face plate. The assembled quick connect fitting is tightened against the pump head by inserting a lever into a passage defined by the cam head so that the longitudinal axis of the lever is at right angles to the longitudinal axis of the cam body. Pivoting of the lever causes the cam to rotate about its longitudinal axis, thereby causing an offset central portion of the cam body to contact the body of the cam follower. The cam follower is thus induced to slide within the face plate towards the pump head, pushing a set screw carried in the cam follower against the center of the pump head body second face. The pressure created as the set screw is forced against the center of the pump head body second face is evenly distributed across the pump head body first face and forms a seal between the pump head body first face and the base plate, while centering the pump head against the base plate to avoid cocking.

Thus, the quick connect assembly of the present invention provides a quick connect pump head assembly for analytical equipment that is rapidly and easily applied and removed. The locating pins of the quick connect assembly serve as support elements that bear the weight of the pump head during removal and installation of the pump head, and which guide the pump head into position on the pump housing without the possibility of damaging the enclosed piston or its seals. Additionally, the quick connect assembly is designed so as to avoid cocking of the sealing surface when the pump head is tightened against the pump. Removal and installation is rapidly effected by loosening the set screw of the first embodiment or pivoting the cam lever of the second embodiment which permits the face plate to be rapidly disengaged from the locating pins for slidable removal of the pump head body.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
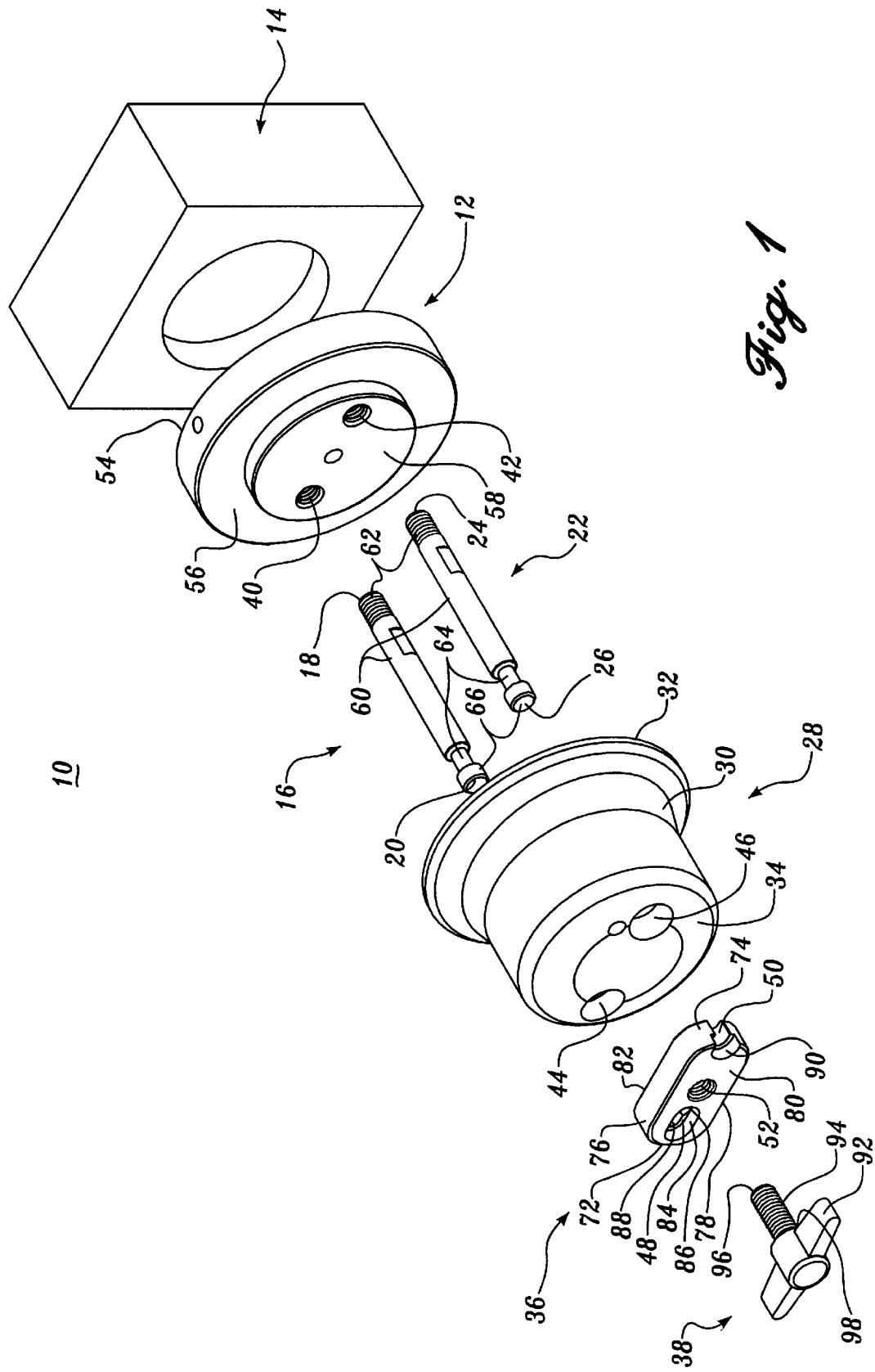
FIG. 1 shows a pictorial exploded view of a first preferred embodiment of the pump head quick connect assembly of the present invention.
Figure 2:
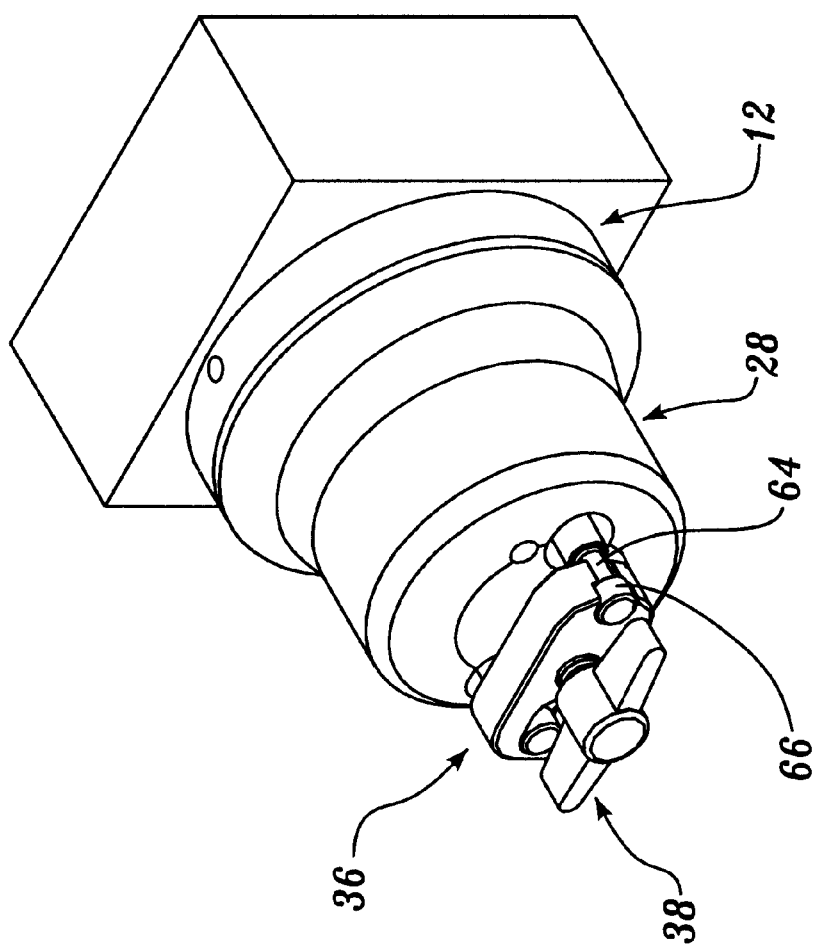
FIG. 2 shows a pictorial view of first preferred embodiment of the pump head quick connect assembly of FIG. 1 in the assembled configuration.

As shown in FIGS. 1 and 2, in a first preferred embodiment of the present invention, the pump head quick connect assembly 10 mounts on a base plate 12 of a pump housing 14, the assembly 10 includes a first locating pin 16 having a proximal end 18 and a distal end 20, a second locating pin 22 having a proximal end 24 and a distal end 26, a pump head 28 having a body 30 which includes a first face 32 and a second face 34, a face plate 36 and a wing screw 38. Proximal end 18 of first locating pin 16 and proximal end 24 of second locating pin 22 are each externally-threaded and are threadably received within a first internally-threaded passage 40 and a second internally threaded passage 42, respectively, defined by base plate 12. When pump head quick connect assembly 10 is assembled, first locating pin 16 and second locating pin 22 are simultaneously slidably received within a first passage 44 and a second passage 46, respectively, each of which are longitudinally defined through pump head body 30 parallel to and on diametrically opposed sides of the central axis of the pump head body 30. Distal end 20 of first locating pin 16 and distal end 26 of second locating pin 22, both extend beyond second face 34 of pump head body 30, and are slidably received within a first outer passage 48 and a second outer passage 50 of face plate 36, and face plate 36 is moved laterally to engage the ends of the locating pins. Wing screw 38 is threadably inserted within a central, internally-threaded passage 52 of face plate 36. As wing screw 38 is rotated, it centrally contacts pump head body second face 34, thereby forcing pump head body first face 32 against base plate 12 while centering pump head body first face 32 against base plate 12 to avoid cocking. Wing screw 38 preferably includes a brass tip (not shown) to prevent galling against the pump head, and thereby ensures accurate centering over time.

With reference again to FIG. 1, base plate 12 is of generally circular shape and has a first face 54 and a second face 56. Base plate second face 56 can be flat or, as illustrated in the preferred embodiment shown in FIG. 1, base plate second face 56 can optionally include a raised circular portion 58 that is smaller in circumference than base plate 12. First internally-threaded passage 40 and second internally-threaded passage 42, of base plate 12, each extend from a second face 56 towards first face 54, and are located within a raised central portion 58 of second face 56. First locating pin 16 and second locating pin 22 are identical and each includes a generally cylindrical center portion 60, an externally-threaded proximal portion 62, a narrow distal portion 64 defined by an annular groove so as to be of smaller diameter than the rest of center portion 60, and a head portion 66 matching the diameter of the center portion 60.

First locating pin 16 is attached to base plate 12 by threadably inserting externally-threaded proximal portion 62 of first locating pin 16 into first internally-threaded passage 40 of base plate 12. Similarly, second locating pin 22 is attached to base plate 12 by screwably inserting externally-threaded proximal portion 62 of second locating pin 22 into second internally-threaded passage 42 of base plate 12. This construction allows locating pins 16, 22 of the present invention to be mounted into base plates 12 of conventional pump assemblies, in place of the threaded bolts normally used, to convert the pump assembly for quick release of the pump head. It will be appreciated that while, in the preferred embodiment of the present invention shown in FIG. 1 and FIG. 2, first locating pin 16 and second locating pin 22 are threadably inserted into base plate 12, first locating pin 16 and second locating pin 22 can be fixedly attached to base plate 12 by any conventional manner, such as a press fit or brazing. This is because the locating pins 16 and 22, once installed, remain stationary during removal and installation of the pump head assembly, unlike the bolts of conventional pump heads.

Once first locating pin 16 and second locating pin 22 are attached to base plate 12, pump head 28 is mounted onto first locating pin 16 and second locating pin 22 by slidably mounting pump head body 28 passages 44, 46 onto first and second locating pins 16, 22. Pump head body 28 is mounted along the length of first locating pin 16 and second locating pin 22 which bear the entire weight of pump head body 28 until pump head body 28 is tightened against base plate 12 as will be described herein. Alternatively, in the embodiment of base plate 12 including a raised center portion 58, pump head body 28 is mounted along the length of first locating pin 16 and second locating pin 22 until raised center portion 58 of base plate 12 is seated within a complementary circular recess [not shown] defined by pump head body 30 within first face 32. Thereafter, most of the weight of pump head body 28 is borne by raised center portion 58 of base plate 12 until pump head body 28 is tightened against base plate 12. When pump head 28 is thus mounted onto first locating pin 16 and second locating pin 22, the narrow distal portions 64 and head portions 66 of first locating pin 16 and second locating pin 22 project beyond pump head body second face 34. While not yet secured to form a seal, the weight of pump head body 28 is supported in this position on the locating pins 16, 22, preventing damage to the pump piston [not shown] received within the pump head body 30.

Once pump head 28 is mounted on first locating pin 16 and second locating pin 22, pump head 28 is selectively and rapidly secured to base plate 12 by means of face plate 36 and wing screw 38. The structure of face plate 36 will now be considered in detail. As shown in FIG. 1 and FIG. 2, face plate 36 has a generally elongate rectangular shape, having a first end 72, a second end 74, an upper surface 76, a lower surface 78, a front face 80 and a rear face 82. First outer passage 48 is located adjacent to first end 72 of face plate 36, and extends from front face 80 to rear face 82. First outer passage 48 is completely surrounded by the face plate 36. First outer passage 48 has an oblong profile when viewed from the direction of front face 80, with the longitudinal axis of the oblate cross-section being coincident with the longitudinal axis of face plate 36. First outer passage 48 includes two portions: a first portion 84 extending from front face 80 towards rear face 82, for approximately one third of the length of first outer passage 48; and a second portion 88 extending from rear face 82 towards front face 80 until it joins first portion 84. First portion 84 is wider than second portion 88 defining a shoulder there between. On the side of first outer passage 48 closest to the center of the face plate 36, a bore 86 is formed which removes the shoulder and enlarges the width of that side of second portion 88 to match the width of first portion 84.

In contrast to first outer passage 48, second outer passage 50 of face plate 36 forms a generally semicircular indentation within end 74 of face plate 36. Second outer passage 50 extends from front face 80 to rear face 82. Second outer passage 50 widens close to front face 80 to form expanded portion 90. In the preferred embodiment shown in FIG. 1 and FIG. 2, expanded portion 90 extends from front face 80 through approximately thirty percent of the length of second outer passage 50, transitioning at an internal shoulder to define a narrower portion 91 continuing to the rear face 82. It is not essential, however, to the utility of first preferred embodiment 10, that second outer passage 50 open onto end 74, nor that first outer passage 48 be disposed with its longitudinal axis coincident with that of face plate 36, as will be apparent with reference to a second preferred embodiment of the present invention to be described subsequently.

Additionally, face plate 36 defines a central passage 52 which is located midway between first outer passage 48 and second outer passage 50 and which extends from front face 80 to rear face 82. Central passage 52 has a circular cross-section, is of uniform diameter and is internally-threaded to adjustably receive wing screw 38.

The assembly of pump head 28, face plate 36 and wing screw 38 is now discussed in detail. After mounting pump head body 28, face plate 36 is attached to pump head 28 by slidably inserting head portion 66 of first and second locating pins 16, 22 into first and second outer passages 48, 50 of face plate 36, so that narrow distal portion 64 and head portion 66 of first locating pin 16 are each enclosed by first outer passage 48. Face plate 36 is then moved laterally so that the narrow distal portion 64 of first locating pin 16 is seated within the narrow outer side of first portion 84 of first outer passage 48, and head portion 66 of second locating pin 22 is seated within the outer side of expanded portion 90 of second outer passage 50. When face plate 36 is so positioned, the distal end 26 and narrow portion 64 of second locating pin 22 is received within second outer passage 50 of the face plate. An inner shoulder defined adjacent the distal end 66 of each locating pin 16, 22 bears against the internal shoulder defined in each of the outer passages 48, 50. Face plate 36 is then securely attached to pump head body 30 by means of wing screw 38. Wing screw 38 includes a transverse head portion 92 and an externally-threaded shaft portion 94 having a proximal end 96 and a distal end 98. Proximal end 96 is fixedly secured to the center of head portion 92 at a right angle to the longitudinal axis of head portion 92.

Externally-threaded tubular portion 94 of wing screw 38 is threadably inserted into internally-threaded central passage 52 of face plate 36. When distal end 98, of shaft portion 94, completely penetrates face plate 36, and contacts pump head body second face 34, head portion 66 of first locating pin 16 and head portion 66 of second locating pin 22 become securely seated within expanded first portion 84, of first outer passage 48, and expanded portion 90, of second outer passage 50, respectively. The pressure created as distal end 98 of wing screw shaft portion 94 is tightened against the center of pump head body second face 34 forces pump head body first face 32 against base plate 12, and centers pump head body 30 against base plate 12 to prevent cocking. FIG. 2 shows an assembled first preferred embodiment of the pump head quick connect assembly 10 of the present invention.

To remove the pump head assembly 10, the procedure is simply reversed. The wing screw 38 is backed off till slightly loose, and the face plate 36 is moved transversely until the distal head portions of the locating pins can pass through the passages of the face plate, at which point the face plate can be removed, followed by the pump head body.

Figure 3:
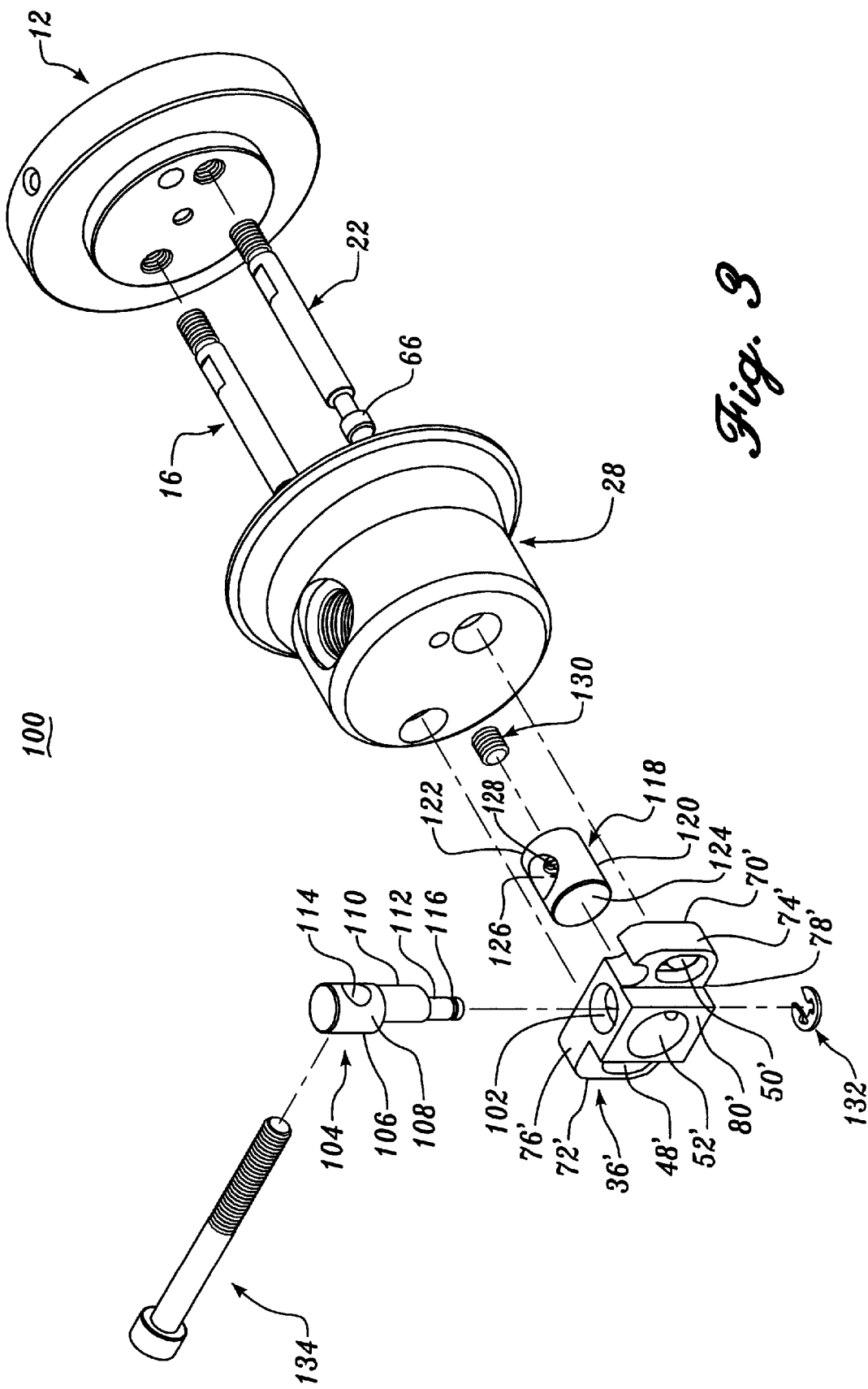
FIG. 3 shows a pictorial exploded view of a second preferred embodiment of the pump head quick connect assembly of the present invention.
Figure 4:
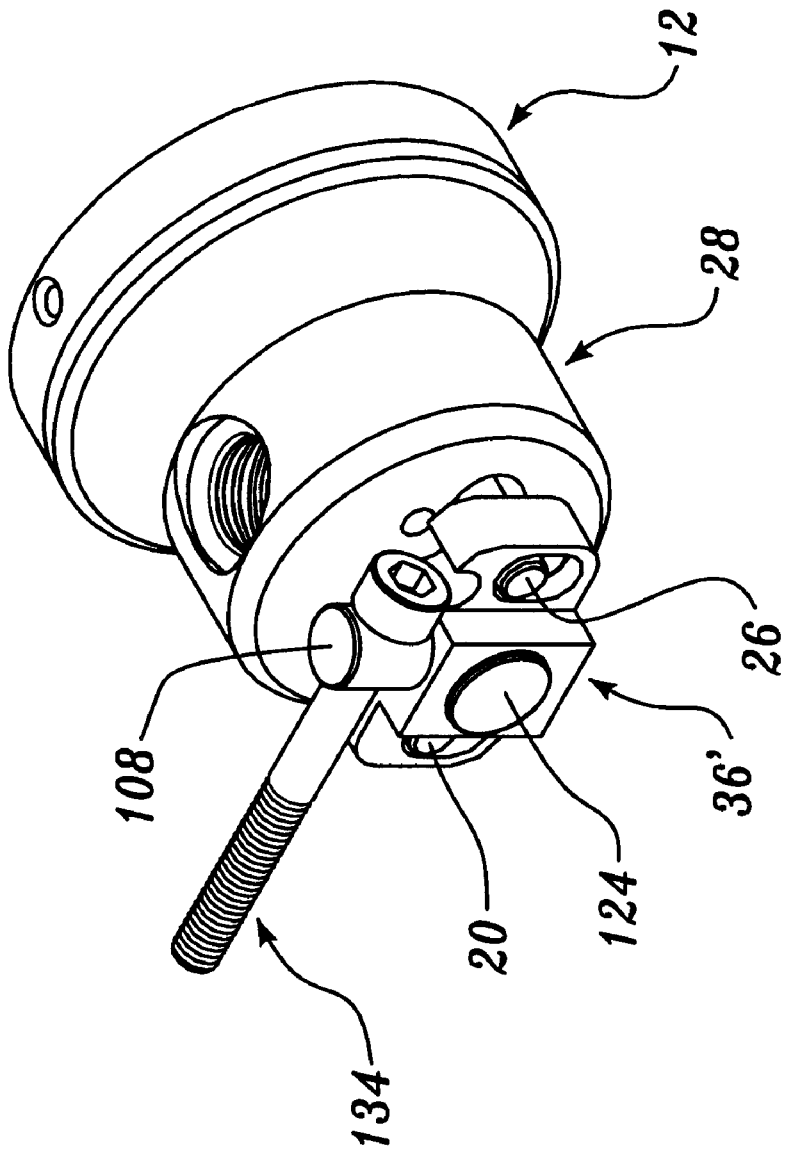
FIG. 4 shows a pictorial view of the second preferred embodiment of the pump head quick connect assembly of FIG. 3 in the assembled configuration.

FIG. 3 shows a second preferred embodiment 100 of the pump head quick connect assembly of the present invention, including a base plate 12, a first locating pin 16, a second locating pin 22 and a pump head 28. The differences between second preferred embodiment 100 and first preferred embodiment 10 reside in the manner of tightening pump head 28 against base plate 12. Consequently, in the subsequent description of second preferred embodiment 100, corresponding features of second preferred embodiment 100 are referred to with the same parts numbers as for first preferred embodiment 10, but with the addition of a prime ('). It should be noted that the styles of base plate 12 and pump head 28 shown in FIG. 3 and FIG. 4 are different from those shown in FIG. 1 and FIG. 2, but the stylistic differences relate to the disposition of a piston within pump head 28 and either style of base plate 12 and pump head 28 may be used in either first preferred embodiment 10 or second preferred embodiment 100 of the present invention. Alternately, base plate 12 can be an integral component of the pump to which pump head 28 is attached.

With reference again to FIG. 3, second preferred embodiment 100 of the pump head quick connect assembly of the present invention includes a face plate 36' having a generally rectangular body 70' having a first end 72', a second end 74', an upper surface 76', a lower surface 78', a front face 80' and a rear face 82'. Face plate body 70' defines a vertical passage 102, extending from the center of upper surface 76' to the center of lower surface 78', which slidably receives an eccentric cam 104. Cam 104 includes a body 106 having a cylindrical head portion 108, an offset (i.e. eccentric) central portion 110 and a cylindrical end portion 112. Head portion 108 has a wider diameter than central portion 110 which, in turn, has a wider diameter than end portion 112. Head portion 108 defines a passage 114 which is oriented perpendicularly with respect to the longitudinal axis of cam body 106. A groove 116 is defined around the circumference of end portion 112.

Vertical passage 102 of face plate body 70' intersects at right angles with central passage 52' of face plate body 70'. Passage 52' is of uniform diameter and is configured to slidably receive a cylindrical cam follower 118. Cam follower 118 includes a body 120 having a proximal end 122 and a distal end 124. Cam follower body 120 defines a vertical passage 126 that completely penetrates cam follower body 120 at right angles to its longitudinal axis. Cam follower body 120 further defines an internally-threaded passage 128 extending from proximal end 122 to vertical passage 126. Internally-threaded passage 128 threadably receives an externally-threaded set screw 130 which projects an adjustable extent beyond cam follower proximal end 122 when fully inserted into passage 128. Set screw 130 preferably includes a brass tip (not shown) to prevent galling.

The assembly of pump head quick connect assembly 100 will now be described in detail. Cam follower 118 is slidably inserted into middle passage 52' of face plate 36' so that vertical passage 126 of cam follower body 120 is aligned with vertical passage 102 of face plate body 70'. Cam 104 is slidably inserted into aligned face plate vertical passage 102 and cam follower vertical passage 126, so that at least groove 116 of end portion 112 is exposed beyond face plate lower face 78', and head portion 108 is outside of face plate upper surface 76'. Cam 104 is retained within face plate body 70' by means of a clip 132 which engages groove 116 of cam body end portion 112 and which, while retaining cam 104 within face plate body 70', permits cam 104 to rotate about its longitudinal axis. Assembled face plate 36', cam 104 and cam follower 118 are then mounted onto pump head 28 by slidably inserting head portions 66 of first and second locating pins 16, 22 into face plate first and second outer passages 48', 50'.

Both first outer passage 48' and second outer passage 50' are both configured similarly to first outer passage 48 of first preferred embodiment 10, except that the oblong axes of the profiles of first outer passage 48' and second outer passage 50' are vertically oriented. Consequently, the internal shoulder of passages 48', 50' extend upwardly towards upper surface 76' of face plate 36'. When face plate 36' is mounted on head portion 66 of first locating pin 16, face plate 36' slides past head portion 66 of first and second locating pins 16, 22, and drops onto grooved portion 64 of the locating pins and is securely seated against the semicircular shoulders of first outer passage 48' and second outer passage 50', respectively. Face plate 36' is dropped down to so engage pins 16, 22, and conversely can be lifted up to disengage the pins 16, 22.

Face plate 36' is securely attached to pump head body 28 by inserting a cap screw 134 or other elongate lever into cam head passage 114 so that the longitudinal axis of cap screw 134 is at right angles to the longitudinal axis of cam 104. Cap screw 134 is rotated, counterclockwise in preferred embodiment 100 shown in FIG. 3, thereby rotating cam 104 and causing cam central offset portion 110 to internally engage the portion of cam follower body 120 closest to cam follower proximal end 122. Consequently, cam follower 118 slides within face plate middle passage 52' causing set screw 130 to engage the center of pump head body second face 34. The pressure created as set screw 130 is tightened against the center of pump head body second face 34 forces pump head body first face 32 against base plate 12 thereby centering pump head body 30 against base plate 12 to prevent cocking. FIG. 4 shows an assembled, second preferred embodiment of the pump head quick connect assembly 100 of the present invention.

It is understood that, while the preferred embodiment of the pump head quick connect assembly 10 shown in FIG. 3 includes a cam 104 actuated by inserting and rotating a cap screw 134, numerous other methods can be used, based on the disclosure contained herein, for rotating cam 104. For example, cam head portion 108 can optionally include a polygonal portion, such as a hexagonal portion, which is engageable by a wrench that can thereby be used to rotate cam 104. Alternatively, a hexagonal recess can be formed within cam head portion 108 which is engageable by an Allen wrench which can thereby be used to rotate cam 104. Further, rather than using a single cam 104, a series of cams could instead be used. Additionally, rather than using a set screw 130, a compression spring or other adjustable mechanism could be utilized.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A quick connect assembly for selectively securing a pump head to the base of a pump of analytical equipment comprising:

first and second locating pins securable to project from the base of the pump;

a pump head that is slidably receivable at least partially over said first locating pin and said second locating pin; and a cross member selectively securable to the first and second locating pins to reversibly secure said pump head to said base.

2. The quick connect assembly of claim 1 wherein the pump head comprises a body defining two longitudinal passages which slidably receive the first and second locating pins.

3. The quick connect assembly of claim 1 wherein the first and second locating pins each have a distal end contoured for releasable engagement with said cross member.

4. The quick connect assembly of claim 3 wherein the cross member comprises a face plate defining first and second apertures that selectively receive the distal ends of the locating pins.

5. The face plate of claim 4 having a body defining a first outer passage and a second outer passage, said first and second outer passages each comprising a wide portion and a narrow portion separated by a shoulder therebetween, said shoulders of said first and second outer passages engaging complementary shoulders defined by said distal ends of said first and second locating pins.

6. The face plate of claim 5 wherein the first and second outer passage shoulders are oriented horizontally with respect to the longitudinal axis of the face plate.

7. The face plate of claim 5 wherein the first and second outer passage shoulders are oriented vertically with respect to the longitudinal axis of the face plate.

8. The face plate of claim 4 further comprising a screw carried on the face plate for tightening the pump head against the base.

9. The face plate of claim 8 wherein the screw is threadedly received within a central passage defined in the face plate and adjustably contacts the pump head.

10. The face plate of claim 4 further comprising a cam, a cam follower and a protuberance defined on the cam follower for selectively contacting the pump head to tighten the pump head against the base.

11. The face plate of claim 10 wherein the cam follower comprises a generally cylindrical body defining a passage that penetrates said body at right angles to its longitudinal axis, said cam follower being slidably received within a face plate central passage so that the cam follower passage is aligned with a vertical passage that penetrates the face plate and intersects at right angles with the central passage of the face plate.

12. The face plate of claim 11 wherein the cam comprises a generally cylindrical body having a head portion, an offset center portion and an end portion, said cam being slidably inserted into face plate vertical passage and aligned cam follower passage.

13. The face plate of claim 12 wherein said cam completely penetrates said face plate body and is retained therein by a clip mounted on said cam end portion which is at least partially external to said face plate.

14. The cam of claim 12 further comprising a passage defined by the head portion, the longitudinal axis of said passage being oriented perpendicularly with respect to the longitudinal axis of the cam, said head portion passage being configured to receive a lever for rotating the cam about its longitudinal axis so that the offset portion of the cam contacts the cam follower body thereby causing the cam follower to slide towards and engage the pump head.

15. The cam follower of claim 12 further comprising an adjustable engagement tip secured to the portion of the cam follower that is closest to the pump head, said engagement tip defining said protuberance and being tightened against said pump head as the cam rotates about its longitudinal axis.

16. A quick connect assembly for a pump head of analytical equipment comprising:
   a base having a first locating pin and a second locating pin projecting therefrom;
   a pump head having a body defining a first passage and a second passage, said body being slidably received on said first and second locating pins with said first and second locating pins passing through said first and second passages; and
   a face plate that selectively connects a portion of said first locating pin to a portion of said second locating pin, said face plate releasably securing said pump head body to said base.

17. A quick connect assembly for a pump head of analytical equipment comprising:
   a base having a first locating pin and a second locating pin projecting therefrom;
   a pump head having a body defining a first passage and a second passage, said first passage slidably receiving said first locating pin and said second passage slidably receiving said second locating pin; and
   a fitting that releasably secures said pump head to said base.

18. A quick connect assembly for a pump head of analytical equipment comprising:
   a base having a first locating pin and a second locating pin projecting therefrom;
   a pump head having a body defining a first passage and a second passage, said first passage receiving said first locating pin and said second passage receiving said second locating pin; and
   a quick release fitting coupling the body to the first and second locating pins to releasably secure the body to the base.

19. A quick connect assembly for selectively securing a pump head to the base of a pump of analytical equipment comprising:
   first and second locating pins securable to project from the base of the pump;
   a pump head that is slidably receivable at least partially over said first locating pin and said second locating pin; and
   a face plate defining a center passage, and first and second outer passages, said first and second outer passages slidably receiving a portion of said first and second locating pins, respectively, and said center passage threadedly receiving a tightening element reversibly tightenable against said pump head thereby releasably securing said pump head to said base.

20. A quick connect assembly for selectively securing a pump head to the base of a pump of analytical equipment comprising:
   first and second locating pins securable to project from the base of the pump;
   a pump head that is slidably receivable at least partially over said first locating pin and said second locating pin;
   a face plate defining first and second outer passages and a vertical passage oriented perpendicular to the first and second outer passages, said first and second outer passages slidably receiving said first and second locating pins, respectively; and
   a cam being rotatably received within said vertical passage of said face plate and a cam follower coupled to said cam, the rotation of said cam inducing horizontal motion of said cam follower towards said pump head thereby causing said cam follower to compressively abut said pump head thereby releasably securing said pump head to said base.

* * * * *